US012751739B2

(12) United States Patent
Truckai et al.

(10) Patent No.: US 12,751,739 B2
(45) **Date of Patent: *Oct. 6, 2026**

(54) MEDICAL DEVICE AND METHOD FOR PREVENTING ADHESIONS

(71) Applicant: Meditrina, Inc., San Jose, CA (US)

(72) Inventors: Csaba Truckai, San Jose, CA (US); John H. Shadduck, San Jose, CA (US)

(73) Assignee: Meditrina, Inc., San Jose, CA (US)

( * ) Notice: Subject to any disclaimer, the term of this patent is extended or adjusted under 35 U.S.C. 154(b) by 147 days.

This patent is subject to a terminal disclaimer.

(21) Appl. No.: 18/931,618

(22) Filed: Oct. 30, 2024

(65) Prior Publication Data

US 2025/0107823 A1 Apr. 3, 2025

Related U.S. Application Data

(60) Continuation of application No. 18/351,375, filed on Jul. 12, 2023, now Pat. No. 12,150,674, which is a division of application No. 17/145,755, filed on Jan. 11, 2021, now abandoned.

(60) Provisional application No. 62/959,686, filed on Jan. 10, 2020.

(51) Int. Cl.

| | |
|---|---|
| ***A61B 17/12*** | (2006.01) |
| ***A61B 17/42*** | (2006.01) |
| *A61B 17/00* | (2006.01) |
| *A61B 90/00* | (2016.01) |

(52) U.S. Cl.

CPC .... *A61B 17/42* (2013.01); *A61B 2017/00557* (2013.01); *A61B 2017/00893* (2013.01); *A61B 2017/00951* (2013.01); *A61B 2017/00995* (2013.01); *A61B 2017/12004* (2013.01); *A61B 2017/4216* (2013.01); *A61B 2090/0816* (2016.02)

(58) Field of Classification Search

CPC .. A61B 2017/4216; A61B 2018/00559; A61B 2018/00577; A61B 17/42; A61B 17/4208; A61B 2017/4225; A61B 2017/4233; A61B 17/4241; A61B 17/425; A61B 17/43; A61B 17/435; A61B 2017/00557; A61B 2017/00893; A61B 2018/0022; A61B 2090/0816; A61M 2210/1433; A61M 25/1002; A61M 2025/105; A61M 2210/1475; A61M 31/002; A61M 2025/1065; A61M 25/10185

See application file for complete search history.

(56) References Cited

U.S. PATENT DOCUMENTS

| | | |
|---|---|---|
| 2006/0089658 A1 | 4/2006 | Harrington |
| 2015/0196300 A1 | 7/2015 | Tischler et al. |
| 2020/0187985 A1 | 6/2020 | Abd Elaal |

(Continued)

FOREIGN PATENT DOCUMENTS

| | | |
|---|---|---|
| CN | 200984216 | 12/2007 |
| WO | WO 2013/033791 | 3/2013 |

OTHER PUBLICATIONS

Aceves et al., "The Extrathyronine Actions of Iodine as Antioxidant, Apoptotic, and Differentiation Factor in Various Tissues", Thyroid, vol. 23, No. 8, 2013.

*Primary Examiner* — Katherine M Shi

(74) *Attorney, Agent, or Firm* — Levine Bagade Han LLP

(57) ABSTRACT

Methods and devices for treatment of a uterine cavity to prevent adhesions following a surgical intervention.

20 Claims, 8 Drawing Sheets

(56) References Cited

U.S. PATENT DOCUMENTS

| | | | |
|---|---|---|---|
| 2021/0212727 | A1 | 7/2021 | Truckai et al. |
| 2023/0355274 | A1 | 11/2023 | Truckai et al. |

MEDICAL DEVICE AND METHOD FOR PREVENTING ADHESIONS

CROSS-REFERENCE TO RELATED APPLICATIONS

This application is a continuation of U.S. application Ser. No. 18/351,375 filed Jul. 12, 2023, which is a divisional of U.S. application Ser. No. 17/145,755 filed on Jan. 11, 2021, now abandoned, which claims benefit of U.S. provisional application No. 62/959,686 filed on Jan. 10, 2020, the entirety of which is incorporated by reference.

BACKGROUND OF THE INVENTION

1. Field of the Invention

The present invention relates to an intra-uterine device adapted for temporary placement in a uterine cavity to prevent adhesions following a surgical intervention.

2. Description of the Background Art

Following a gynecological procedure or surgery, such as a myomectomy, polyp removal, ablation, curettage or another uterine surgery, a frequent complication are post-surgical adhesions between anterior and posterior walls of the uterus.

SUMMARY

The present disclosure includes methods and devices for treating a uterine cavity. For example, the treatment can include a uterine cavity that is injured following a medical procedure or other trauma that causes bleeding therein. In one example, a method for treating a uterine cavity includes deploying a device within the uterine cavity in a delivery profile, the device having a contact surface carrying a first pharmacological agent; expanding the device to cause the contact surface to move into an expanded profile where the contact surface engages a surface of the uterine cavity to tamponade a bleeding at the surface of the uterine cavity and such that the first pharmacological agent releases from the contact surface into the surface of the uterine cavity over a first interval; collapsing the device to a collapsed profile to provide a barrier between uterine cavity surfaces wherein a second pharmacological agent releases from the contact surfaces over a second interval; and removing the device after the second interval.

Variations of the method can include a second interval that begins after a first interval ends. Alternatively, the intervals can overlap or can be spaced in time.

The first pharmacological agents can be selected from a group constating of a hemostatic agent, an analgesic agent, an anti-cramping agent, and a non-steroidal anti-inflammatory agent. The second pharmacological agent can be selected from a group consisting of an anti-adhesion agent, an analgesic agent, an anti-cramping agent, and a non-steroidal anti-inflammatory agent. However, the disclosure includes the use of any pharmacologic, biologic, or medicinal agent as needed.

As noted above, the uterine cavity can include one or more regions of tissue that are damaged, including but not limited to tissue that is damaged after a therapeutic procedure. Such procedures can include resection, curettage and/or ablation of tissue.

In an additional variation of the method deploying the device includes trans-cervically introducing an elongate introducer into the uterine cavity and deploying the device from a passageway in the elongate introducer.

Variations of the methods and device can include deploying the device using a spring-like element in the device to expand the device to a triangular shape in the uterine cavity.

In an additional variation of methods described herein include deploying the device includes removing introducer from a uterus and a cervix and leaving a tether extending through a cervical canal, where the tether is connected to the device.

Expanding the device can include inflating the device with a fluid injected through a lumen of a tether coupled to an interior chamber of the device. However, any inflation or expansion means is within the scope of this disclosure. Once expanded, the device can be maintained in the expanded position by sealing the lumen of the tether. Additional variations of the tether can include an actuatable a stop mechanism in a portion of the tether outside the uterine cavity, inside the uterine cavity, or at any location relative to the device. In such cases, releasing the device to reduce the expanded profile can comprise actuating the stop mechanism to unseal the lumen.

Additional pharmacological agents can be dispensed through a second tether channel into the uterine cavity.

In an additional variation, the device can be removed from the uterine cavity after the second interval. For example, removal can occur by pulling a tether or other structure coupled to the device outwardly from a cervical canal and uterine cavity.

The present disclosure further includes devices configured for temporary implantation in a uterine cavity following a medical procedure therein. For example, such a device can include a tissue contacting structure being moveable between a deployment configuration, a collapsed, configuration, and an expanded configuration in which the tissue contacting structure engages a surface of the uterine cavity; where the tissue contacting structure comprises a thin film member disposed around a spring element; and at least one pharmacological agent located on or in the thin film member and configured to be releasable from a surface of the thin film member over a time release interval.

Variations of the device can include a thin film member that has a fluid tight interior chamber to allow inflation of the thin film member. As noted above, the devices can include one or more tethers for inflation, delivery of substances, and/or retrieval of the device from the uterine cavity. Moreover, one or more of the tethers can include an inflation balloon therein adapted for coupling to an inflation source.

DETAILED DESCRIPTION OF THE INVENTION

Figure 1:
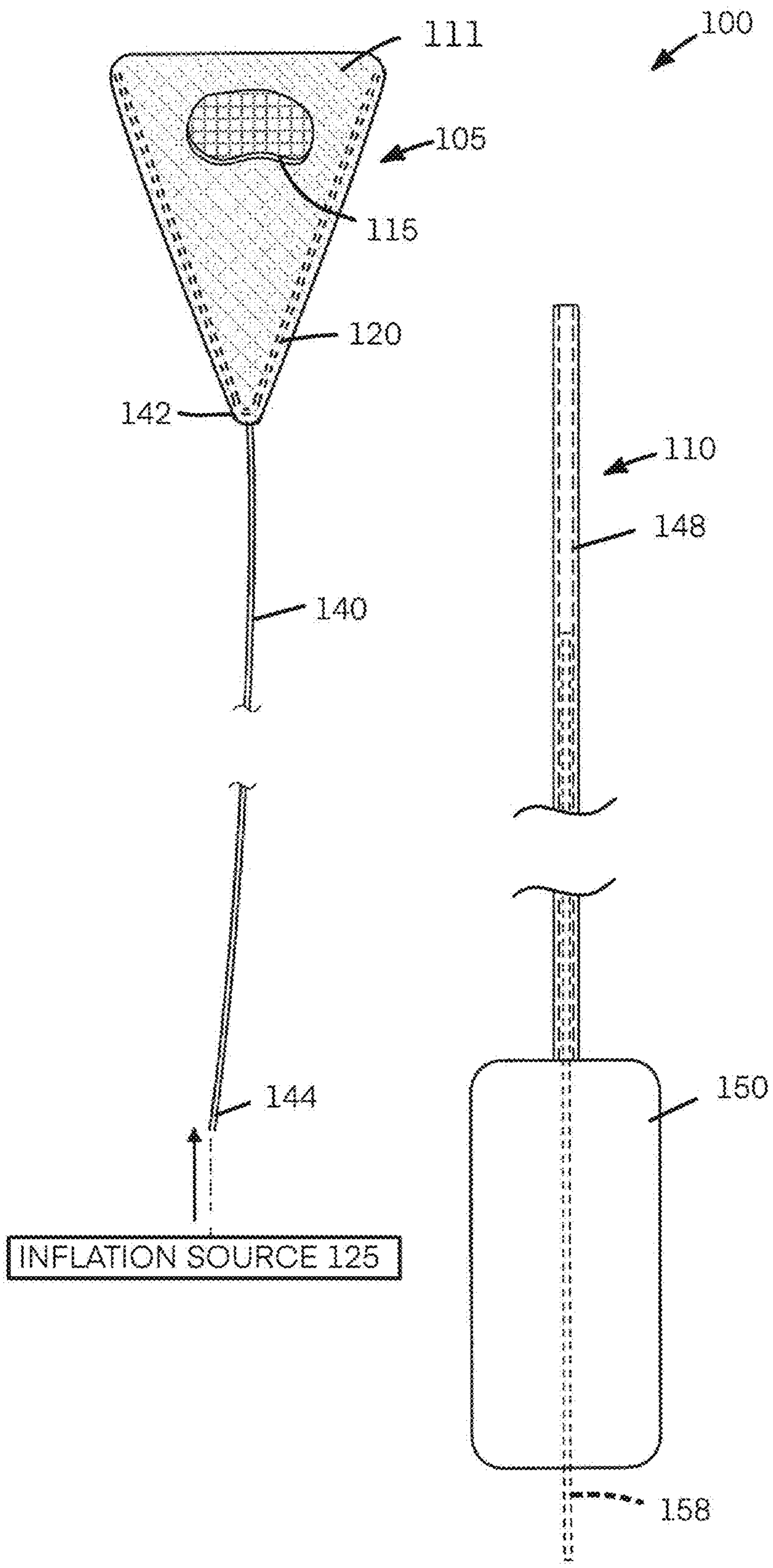
FIG. 1 illustrates a variation of the present invention which consists of an expandable-collapsible anti-adhesion device adapted for temporary deployment in a patient's uterus together with an introducer that is configured for trans-cervical introduction of the anti-adhesion device int a patient's uterus.

Referring to FIG. 1, in anti-adhesion system 100 corresponding to the present invention is shown which consists of an expandable-collapsible device 105 and an elongate introducer 110. The anti-adhesion device 105 when expanded and deployed in a patient's uterus has drug-delivery surfaces 111 that engage and contact the walls 112 of the patient's uterus 114 (see FIG. 3C). In one variation, the anti-adhesion device 105 consists of a thin film member 115 that can be elastomeric or non-elastomeric and is laterally expandable from a collapsed state to an expanded state by an interior spring element 120. In one variation, the spring element 120 is a wire or flat ribbon member that has resilient spring characteristics capable of expanding the thin film member 115 to its expanded state or shape.

In the variation shown in FIG. 1, the thin film member 115 surrounds the spring element 120 and comprises an inflatable structure, which can be inflated and expanded by a liquid or gas from an inflation source 125 following deployment in a patient's uterus. As can be seen in FIG. 1, a tether 140 is coupled to a proximal end 142 of the thin wall member and device 105. In one variation, the tether 140 is tubular and has an interior lumen 144 for coupling to the inflation source 125 for inflating the anti-adhesion device. Thus, the spring element 120 can assist in the lateral expansion of the anti-adhesion device 105 and the inflation source 125 can further assist in expanding the thickness of the device 105 to ensure contact of the outer surface 111 of the thin film member 115 with the uterine cavity walls for tamponading the uterine cavity wall following a resection procedure.

Figure 3A:
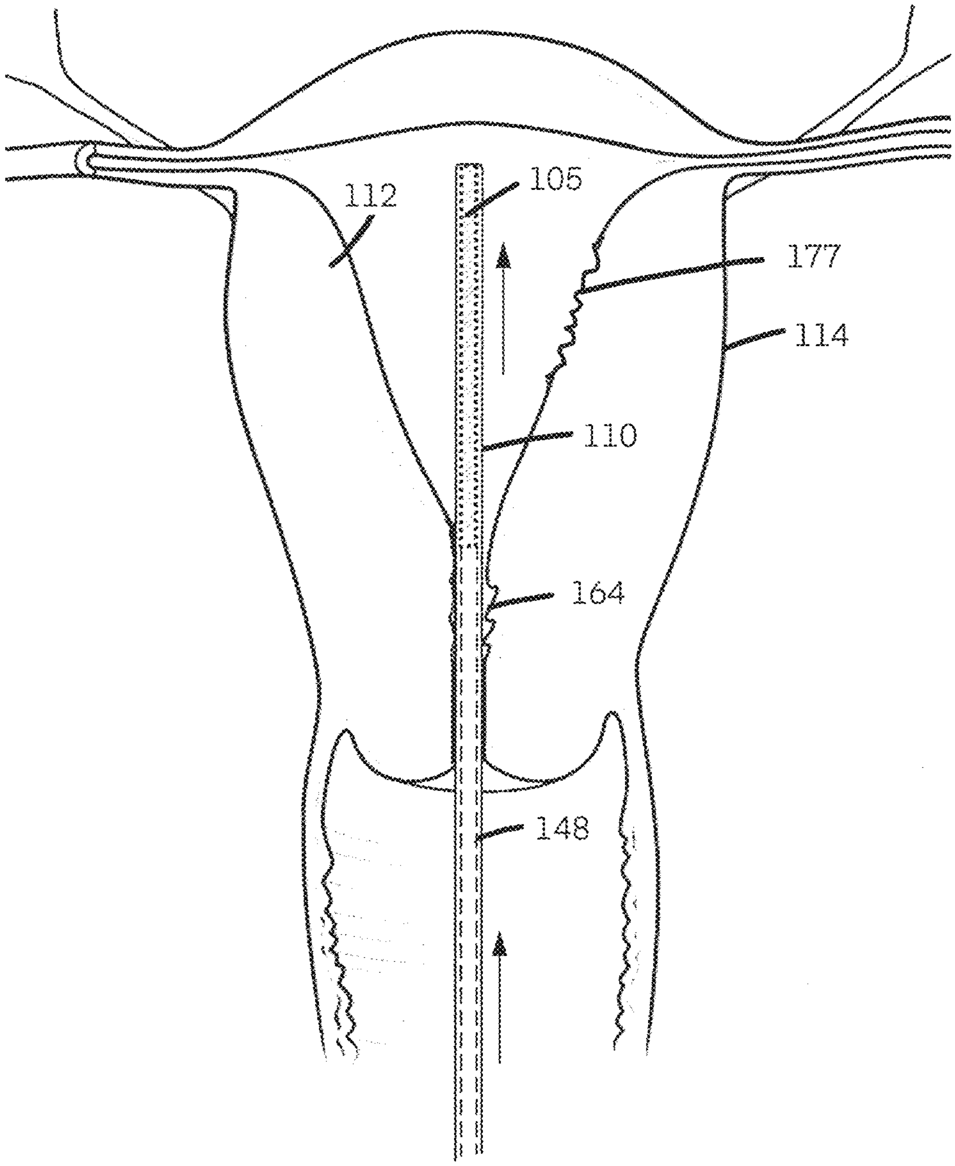
FIG. 3A is a subsequent view of the patient's uterus as in FIGS. 2A-2B after removal of the endoscope and resection device further showing initial step in the method of the invention which consists of the trans-cervical introduction of an elongated introducer sleeve of the present invention that carries a deployable anti-adhesion device.

Still referring to FIG. 1, it can be understood that the anti-adhesion device 105 can be collapsed and carried in the interior passageway 148 of a thin wall introducer member 110. Further, the introducer 110 has a handle 150 and carries an internal pusher member or rod 158 for pushing the anti-adhesion device 105 outwardly from the interior passageway 148. As will be described below, the manual withdrawal of the introducer 110 while maintaining the pusher member 158 in place can be used to deploy the anti-adhesion device 105 in the patient's uterus. In one variation, the elongated introducer 110 consists of a sleeve fabricated of a plastic or metal having a length suited for extending through the patient's cervical canal 164 and the length of the uterine cavity 114 (FIG. 3A). The outer diameter of the introducer 110 can be 5 mm or less and is often 3 mm in diameter or less.

The anti-adhesion device 105 is adapted to perform multiple functions which may be necessary to prevent or eliminate the potential for adhesions in a patient's uterus following a surgical procedure such as a myomectomy, polyp removal, ablation or other surgical treatment. In a first aspect of the invention, the inflation of the thin film member 115 can be used as a tamponade in the uterus following a resection procedure as will be described further below.

In a second aspect of the invention, the outer surface of the thin film layer and edges of the device carry at least one pharmaceutical agent adapted to provide a hemostatic effect. More in particular, the outer surface of the thin film member 115 is adapted for time-release of the hemostatic agent(s) within a 24-hour period following deployment in the patient's uterus. Such hemostatic agents or coagulants may act on blood coagulation pathways in different manners to prevent or promote blood clot formation, many of which are known in the art. The controlled, timed-release aspect of the invention can be provided by any bioerodible, dissolvable, or bioresorbable coating on the device that carries the hemostatic agents.

In a third aspect of the invention, the outer surface of the thin film member carries one or more additional pharmaceutical agents there are adapted to provide at least one of an anti-inflammatory effect, pain relief, or an anti-cramping effect. Anti-inflammatory drugs such as NSAIDs well known in the art. These agents are adapted for release from the surface of the device within an interval ending after 72 hours following deployment in the patient's uterus. The time release aspect again can be provided by leaders of the bioerodible, bioabsorbable or resorbable coatings on the thin film member.

In another aspect of the invention, the outer surface of the anti-adhesion device 105 can carry one or more other pharmaceutical agents adapted to provide anti-cramping that extend to 28 days following deployment in a patient's uterus. In other words, the coatings on the surface of the thin film member can include 2 or 3 different layers that offer time release of different pharmacological agents over time.

Figure 2A:
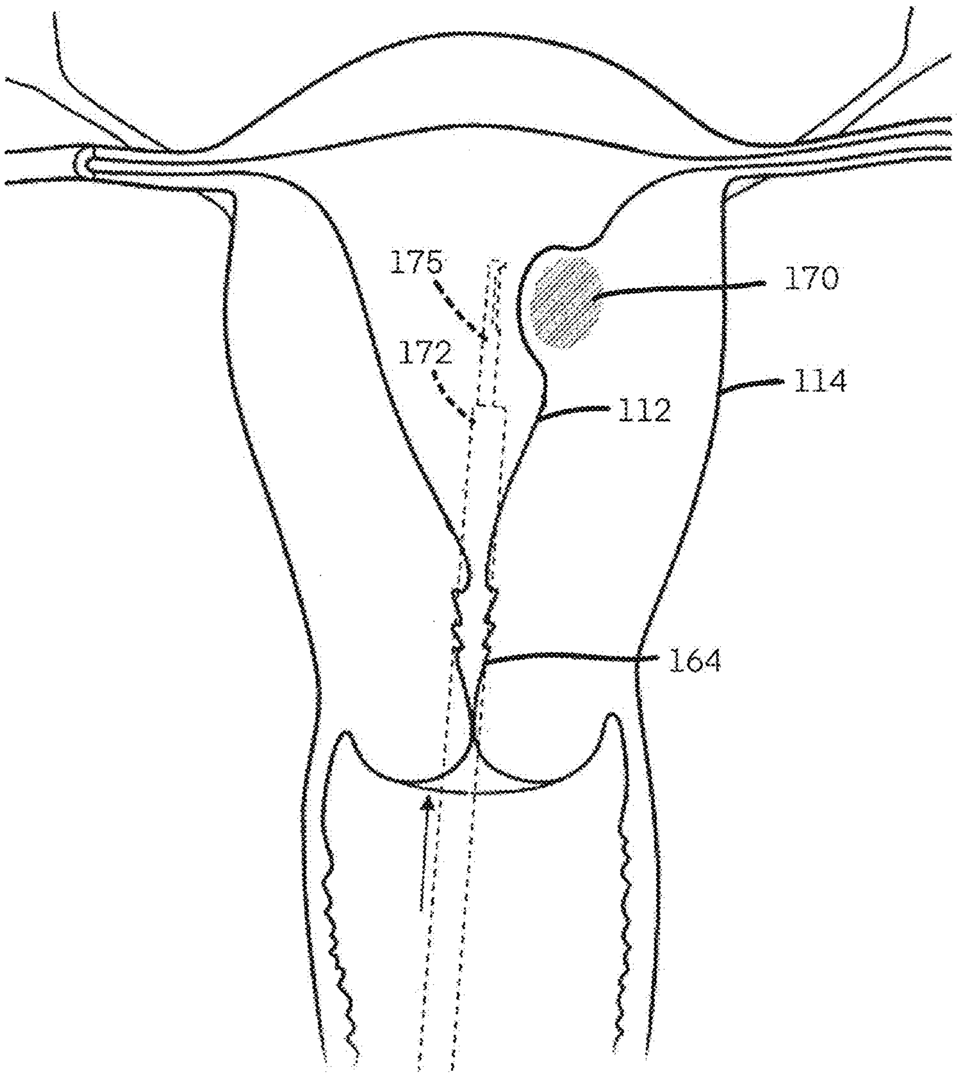
FIG. 2A is a schematic view of the patient's uterus with the fibroid in the uterine wall, and an endoscope and resection device in phantom view introduced through the cervical canal into the uterine cavity to resect the fibroid in a myomectomy procedure.
Figure 2B:
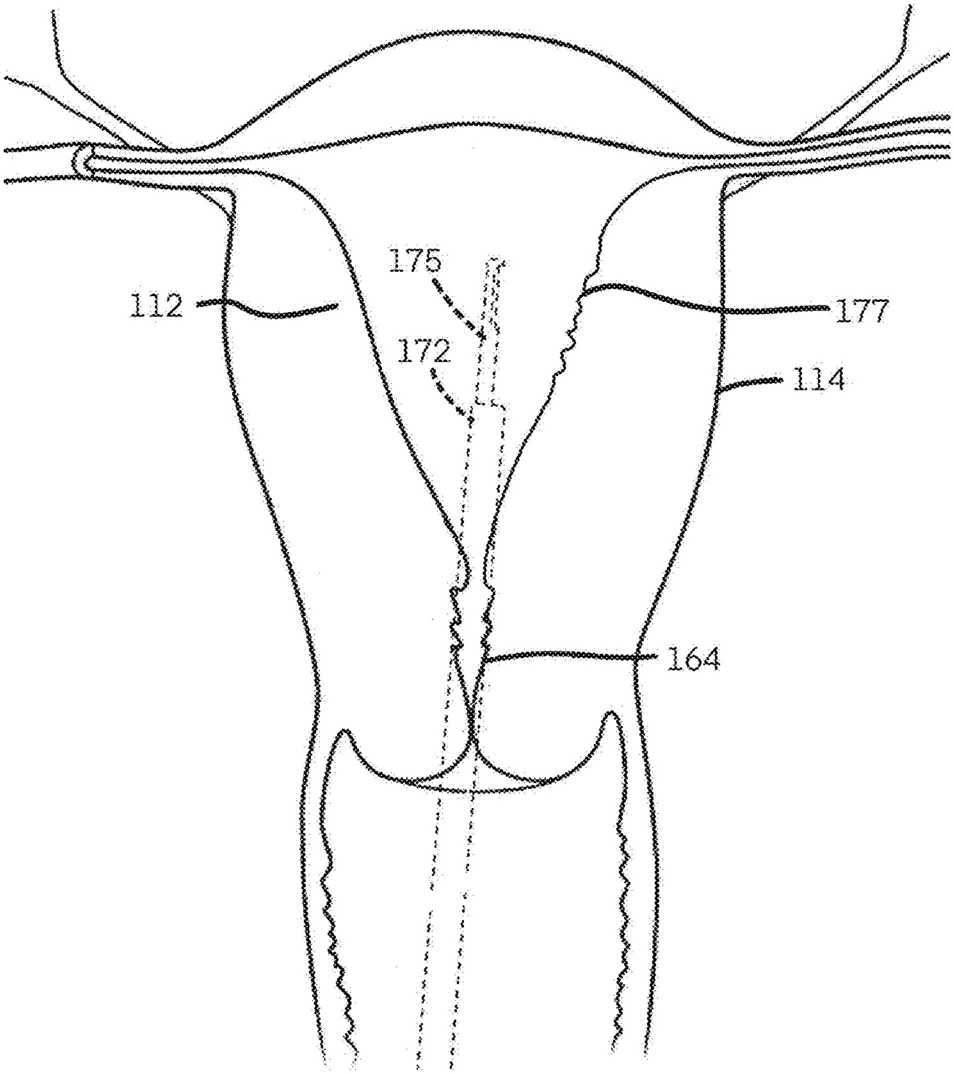
FIG. 2B is a subsequent view of the patient's uterus after the fibroid has been resected with the resecting device, again shown in phantom view.

Now turning to FIGS. 2A-2B and FIGS. 3A-3E, a number of steps relating to a method of the invention are illustrated. FIG. 2A is a schematic sectional view of a patient's uterus 115 with a fibroid 170 in the uterine wall 112. In FIG. 2A, an endoscope 172 and resection device 175 are shown in phantom view introduced through the cervical canal 164 into the uterine cavity to resect the fibroid 170 in a myomectomy procedure. The resection device 175 can be a tubular cutter is known in the art. FIG. 2B is a subsequent view of the patient's uterus 114 after the fibroid 170 has been resected with the resecting device, indicating a resected wall surface 177 that may be bleeding. The endoscope 172 and resection device 175 are again shown in phantom view.

Figure 3B:
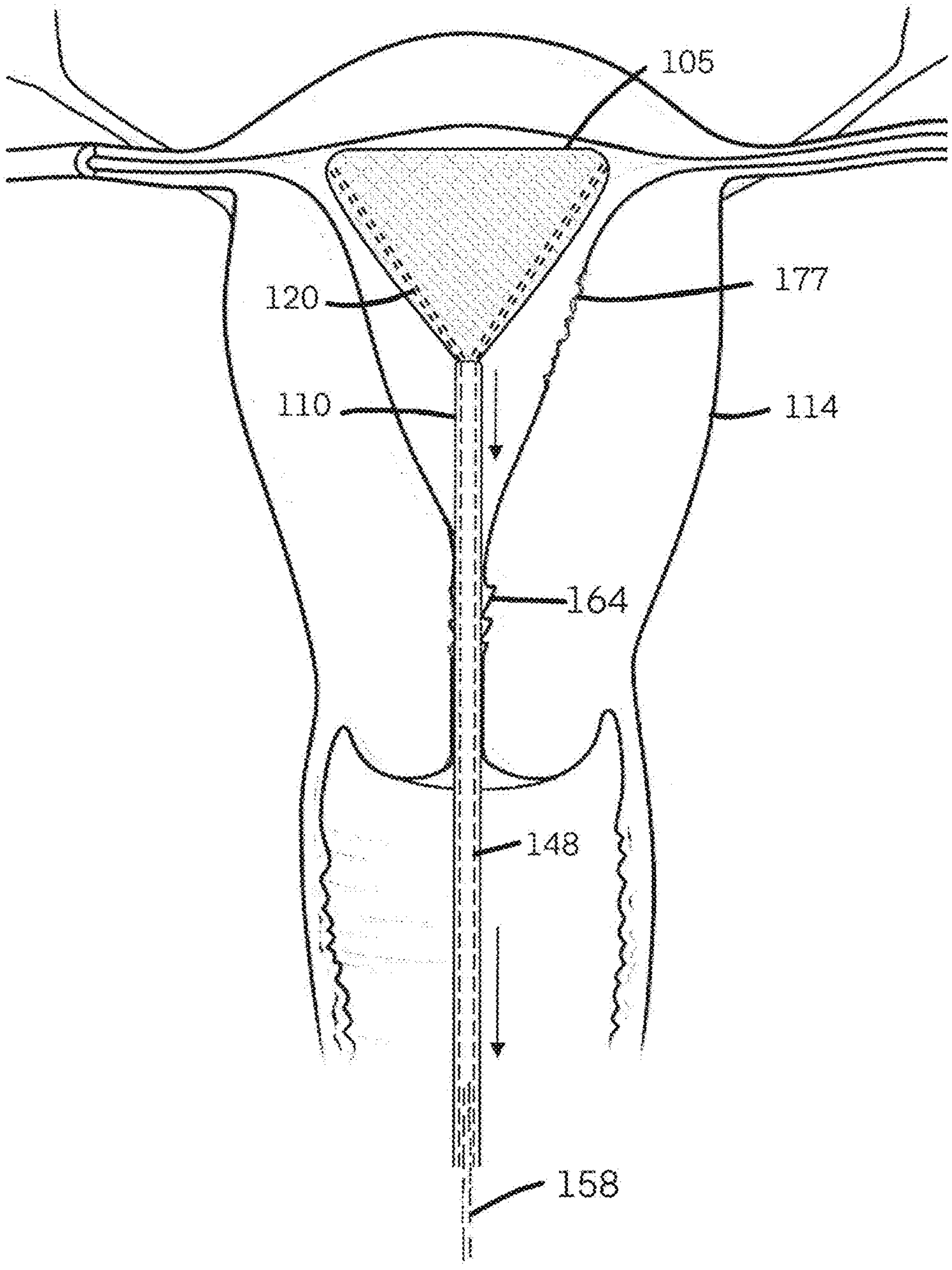
FIG. 3B illustrates another step of the invention comprising an initial stage of the deployment of the anti-adhesion adhesion device of the invention, wherein the introducer sleeve is withdrawn to deploy the anti-adhesion device.

Now referring to FIGS. 3A-3E, the steps of a method of the invention are illustrated. In FIG. 3A, the elongate introducer 110 carrying the collapsed anti-adhesion device 105 is introduced through the patient's cervical canal 164 into the patient's uterine cavity. In FIG. 3B, it can be seen that the elongate introducer 110 is withdrawn in the proximal direction while the pusher member or rod 158 is held stationary which deploys the anti-adhesion device 105 outwardly from the distal tip 182 of the introducer 110.

Figure 3C:
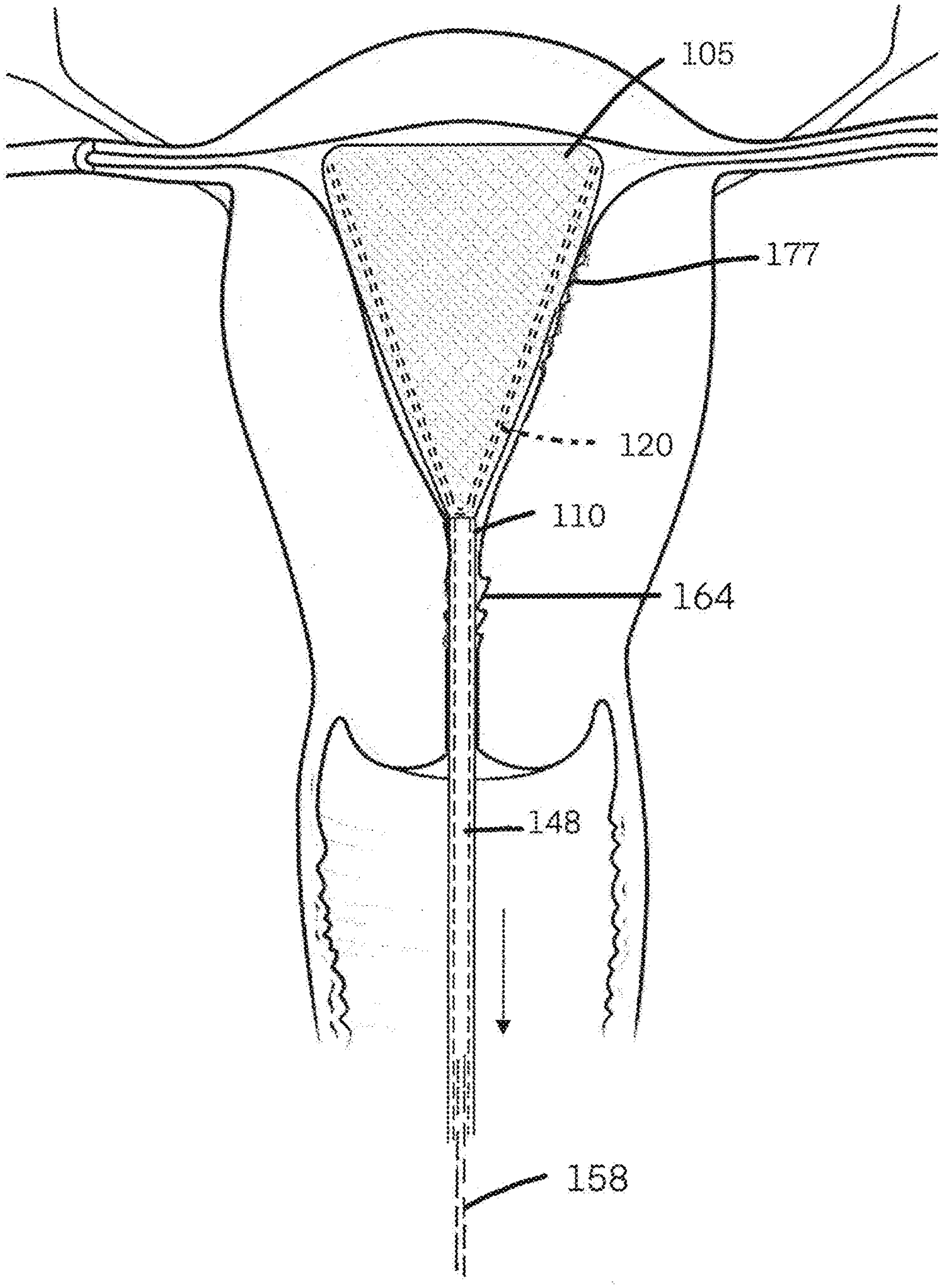
FIG. 3C illustrates a subsequent step of the invention comprising the full deployment of the anti-adhesion adhesion device following further retraction of the introducer sleeve into the cervical canal.

Now turning to FIG. 3C, introducer 100 is fully retracted and the pusher rod 158 remains stationary to thereby fully deploy the device 105 outwardly from the distal tip 182 of the introducer 110. FIG. 3C that shows the anti-adhesion device 105 fully deployed with the spring member 120 expanding the device into its triangular shape in the uterine cavity.

Figure 3D:
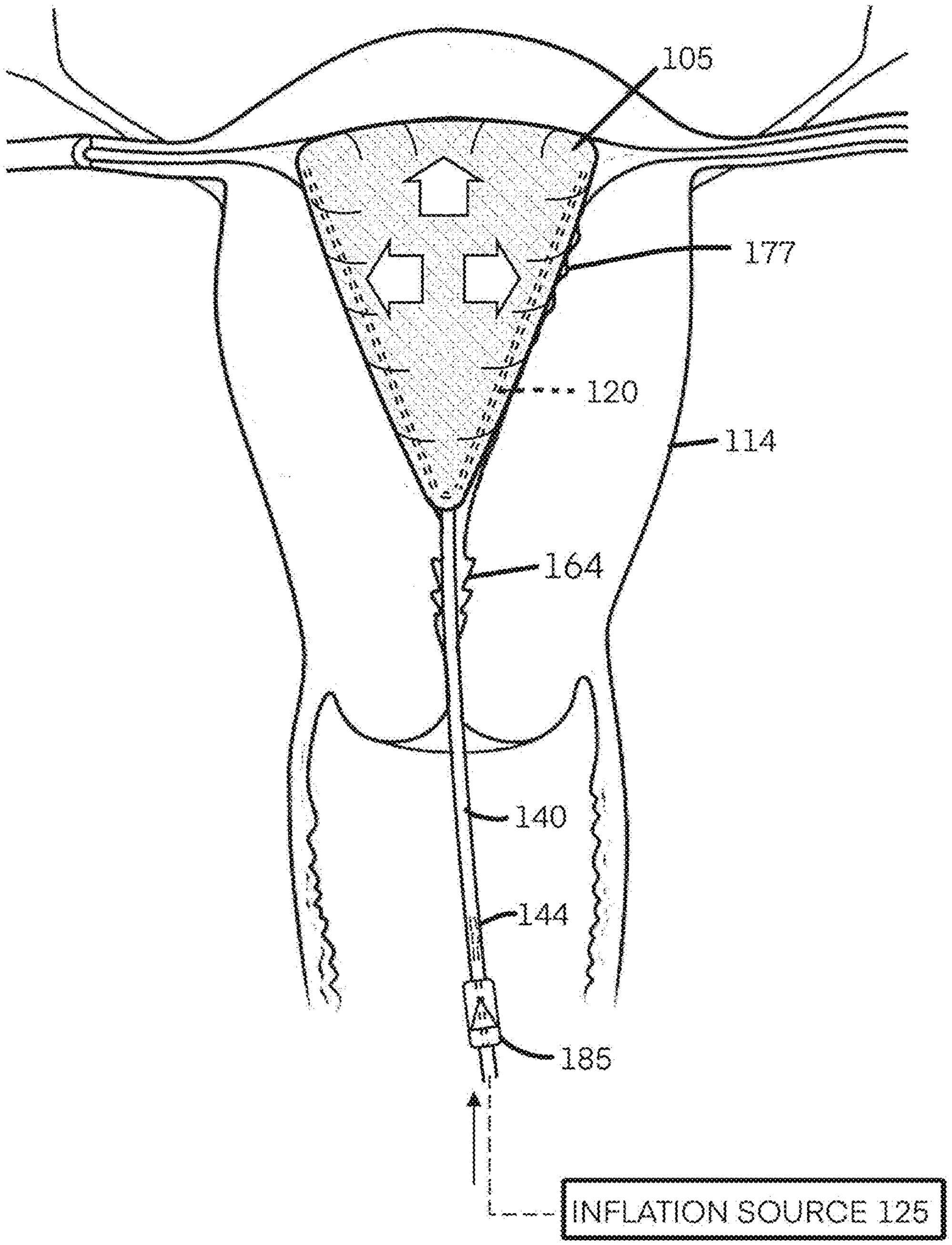
FIG. 3D illustrates a subsequent step of the invention comprising the deployment of the anti-adhesion adhesion device following removal of the introducer sleeve altogether which leaves a tether in place, and the further step of inflating the anti-adhesion device.

FIG. 3D next shows the anti-adhesion device 105 deployed with the introducer 110 completely removed from the patient's body which thereby leaves a tubular tether 140 extending from the device through the cervical canal 164 and cervix to the exterior of the patient's body. Thereafter, an inflation source 125 is connected to the tubular tether 140. In one variation the tether is highly elongated and extends through the passageway 148 in the introducer 110 and handle 150 together with the pusher rod 158. In other variations, the tether 140 can be carried on the outside of the introducer 110. Further, it should be appreciated that the tubular tether 140 which is adapted for fluid expansion or inflation of the device 105 can be independent and detachable from the device 105 after inflation of the device. In such a case, where the tubular tether 140 is removable, another thread-like tether can be provided for later withdrawal of the device 105 from the uterine cavity.

FIG. 3D then further illustrates the inflation source 125 that is coupled to the tubular tether 140 to inflate the anti-adhesion device 105. The expansion of the device 105 and uterine cavity can serve as a tamponade to stop any bleeding at the treatment site. In the deployed position of FIG. 3D, the coatings on the device can erode or dissolve stepwise, or layer by layer, with the first pharmacological component of the invention (hemostatic agents) being bioavailable immediately and then terminating after 12 to 24 hours following deployment.

After a first-time interval, which may be from 3 hours to 24 hours, the inflated anti-adhesion device 105 can be deflated through a valve 185 or pressure release mechanism at the proximal end of the tubular tether 140. Thereafter, the flattened but still laterally expanded anti-adhesion device 105 can remain in the patient's uterus 114 for a subsequent time interval that can extend to 15 days or to 30 days after deployment. Most often, the device would remain deployed for a period of time ranging from 7 days to 30 days. During such a third time interval, the coatings would provide for timed release of additional anti-cramping drugs as described above.

Figure 3E:
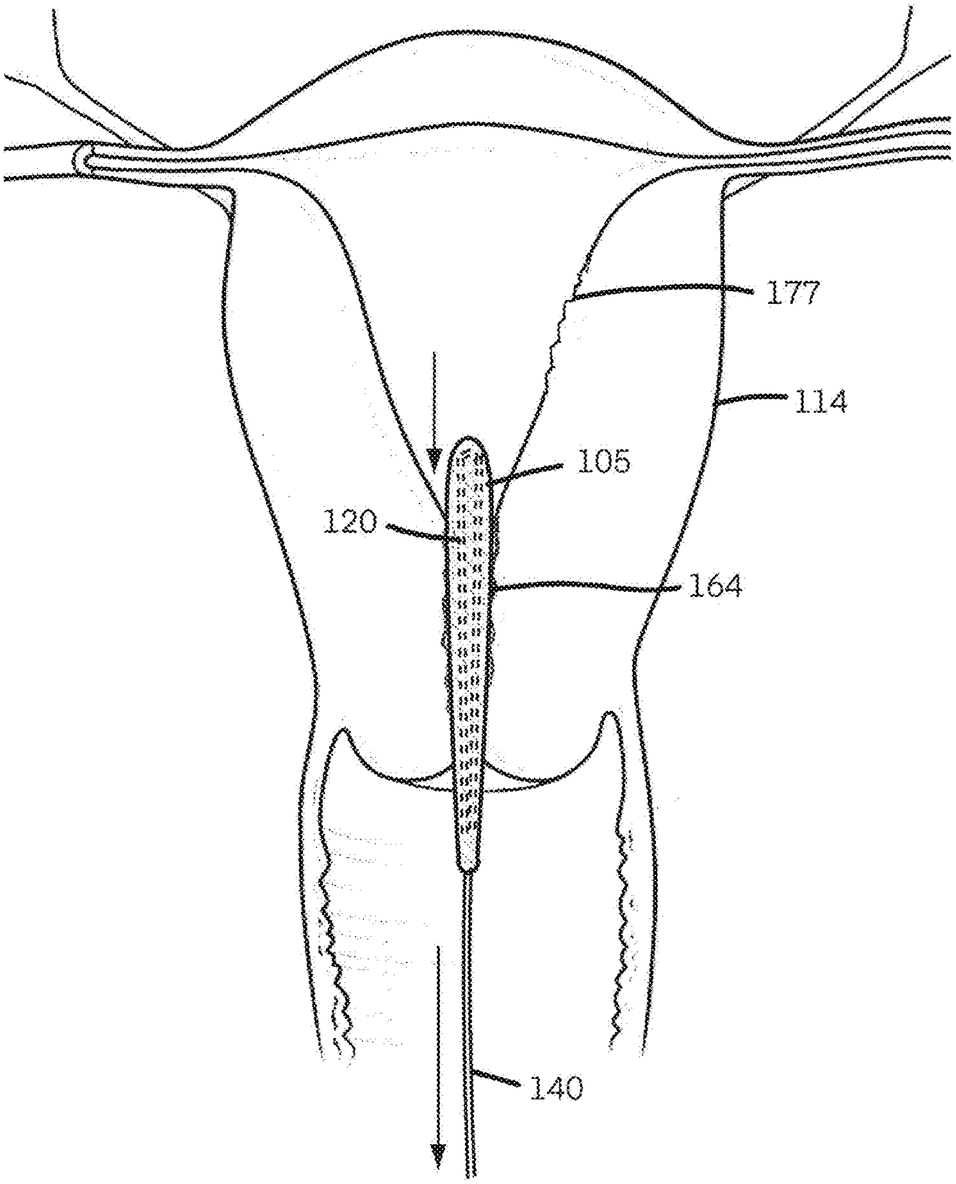
FIG. 3E illustrates a final step in a method of using the invention which comprising pulling on tether to remove the anti-adhesion device from the patient's uterus.

Thereafter, referring to FIG. 3E, the anti-adhesion device 105 can be removed from the uterus 114 by pulling on the tether 140 which collapses the spring member 120 and the thin film member 115 to allow its withdrawal through the cervical canal 164. Generally, method of the invention prevents adhesions by positioning a mechanical member between walls of the uterus so they cannot adhere to one another, by providing a tamponading effect immediately following the surgery, and by pharmacological agents in a timed-release manner to ensure that adhesions do not occur.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of treating a uterine cavity following a medical procedure therein, the method comprising:

deploying a device within the uterine cavity in a delivery profile via an elongate introducer, the device having a contact surface carrying a first pharmacological agent;

withdrawing the elongate introducer in a proximal direction;

inflating the device to an expanded profile where the contact surface of the device engages a surface of the uterine cavity, wherein the device comprises a spring element configured to expand the device into the expanded profile such that the first pharmacological agent releases from the contact surface into the surface of the uterine cavity over a first time interval;

flattening the device to a partially collapsed profile to provide a barrier between uterine cavity surfaces wherein a second pharmacological agent releases from the contact surface over a second time interval, wherein the device is laterally expanded in the partially collapsed profile; and removing the device in a removal profile after the second time interval.

2. The method of claim 1, where the second time interval begins after the first time interval ends.

3. The method of claim 1, wherein the first pharmacological agent is selected from a group constating of a hemostatic agent, an analgesic agent, an anti-cramping agent, and a non-steroidal anti-inflammatory agent, wherein the second pharmacological agent is selected from a group consisting of an anti-adhesion agent, an analgesic agent, an anti-cramping agent, and a non-steroidal anti-inflammatory agent.

4. The method of claim 1, wherein the uterine cavity comprises an area of damaged tissue produced by a therapeutic procedure, wherein the area of damaged tissue is produced by a procedure selected from a group consisting of resection, curettage and ablation.

5. The method of claim 1, wherein deploying the device includes trans-cervically introducing the elongate introducer into the uterine cavity and deploying the device from a passageway in the elongate introducer.

6. The method of claim 5, wherein deploying the device includes allowing the spring element in the device to expand the device to a triangular shape in the uterine cavity.

7. The method of claim 6, wherein the device comprises a thin film member disposed around the spring element, the thin film member has a fluid tight interior chamber to allow inflation of the thin film member.

8. The method of claim 7, wherein deploying the device includes removing the elongate introducer from a uterus and a cervix and leaving a tether extending through a cervical canal, where the tether is connected to the device, wherein the tether is configured such that pulling on the tether, when the device is positioned in the uterine cavity, collapses the spring element and the thin film member to withdraw the device from the uterine cavity.

9. The method of claim 1, further comprising inflating the device with a fluid injected through a lumen of a tether coupled to an interior chamber of the device.

10. The method of claim 9, further comprising a pusher coupled to the tether, the pusher configured to be held stationary during deployment of the device.

11. The method of claim 9, where the tether is detachable from the device.

12. The method of claim 9, further comprising maintaining the device in the expanded profile for the first time interval by sealing the lumen of the tether.

13. The method of claim 12, wherein sealing the lumen of the tether comprises actuating a stop mechanism in a portion of the tether outside the uterine cavity.

14. The method of claim 13, wherein releasing the device comprises actuating the stop mechanism to unseal the lumen.

15. The method of claim 9, further comprising a valve at a proximal end of the tether, wherein the valve is configured to seal a lumen of the tether.

16. The method of claim 15, wherein the device is configured to be deflated to the collapsed profile through the valve.

17. The method of claim 1, further comprising injecting at least one additional pharmacological agent through a tether channel into the uterine cavity.

18. The method of claim 1, wherein removing the device comprises pulling a tether coupled to the device outwardly from a cervical canal and the uterine cavity.

19. The method of claim 1, wherein the first time interval is between 3 hours to 24 hours, and wherein the second time interval is between 1 day to 30 days.

20. A method of treating a uterine cavity following a medical procedure therein, the method comprising:

deploying a device within the uterine cavity in a delivery profile via an elongate introducer, the device having a contact surface carrying a first pharmacological agent;

withdrawing the elongate introducer in a proximal direction;

inflating the device to an expanded profile where the contact surface of the device engages a surface of the uterine cavity;

flattening the device to a partially collapsed profile to provide a barrier between uterine cavity surfaces wherein a second pharmacological agent releases from the contact surface over a second time interval, wherein the device is laterally expanded in the partially collapsed profile; and removing the device in a removal profile after the second time interval, wherein removing the device comprises pulling a tether coupled to the device outwardly from a cervical canal and the uterine cavity.

* * * * *